United States Patent
Fleck et al.

(10) Patent No.: US 7,083,474 B1
(45) Date of Patent: Aug. 1, 2006

(54) SYSTEM FOR LEAD RETENTION AND SEALING OF AN IMPLANTABLE MEDICAL DEVICE

(75) Inventors: Christopher Fleck, Canyon Country, CA (US); Buehl E. Truex, Glendora, CA (US); Russell Klehn, Valencia, CA (US); Anna Barlow, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 11/008,675

(22) Filed: Dec. 8, 2004

(51) Int. Cl.
*H01R 24/04* (2006.01)
*H01R 27/00* (2006.01)

(52) U.S. Cl. ..................... 439/668; 439/218; 439/669
(58) Field of Classification Search ............. 439/909, 439/352, 668, 669, 218, 46, 48; 607/116, 607/37
See application file for complete search history.

(56) References Cited

U.S. PATENT DOCUMENTS

| | | | |
|---|---|---|---|
| 5,012,807 A | 5/1991 | Stutz, Jr. ............... 128/419 P |
| 5,076,270 A | 12/1991 | Stutz, Jr. ............... 128/419 P |
| 5,413,595 A | 5/1995 | Stutz, Jr. ................... 607/637 |
| 5,545,188 A | 8/1996 | Bradshaw et al. ........... 607/37 |
| 6,112,121 A | 8/2000 | Paul et al. ................... 607/37 |
| 6,198,969 B1 | 3/2001 | Kuzma ...................... 607/37 |
| 6,321,126 B1 | 11/2001 | Kuzma ..................... 607/137 |
| 6,755,694 B1* | 6/2004 | Ries et al. .................. 439/668 |
| 6,817,905 B1 | 11/2004 | Zart et al. .................. 439/736 |
| 6,895,276 B1* | 5/2005 | Kast et al. .................... 607/37 |
| 2003/0073348 A1 | 4/2003 | Ries et al. .................. 439/578 |
| 2004/0064164 A1* | 4/2004 | Ries et al. .................... 607/37 |
| 2005/0137642 A1 | 6/2005 | Zart et al. .................... 607/37 |
| 2005/0137665 A1* | 6/2005 | Cole ......................... 607/116 |
| 2005/0186829 A1* | 8/2005 | Balsells ..................... 439/352 |

FOREIGN PATENT DOCUMENTS

| | | |
|---|---|---|
| EP | 0 339 877 A2 | 4/1989 |
| EP | 0 339 877 A3 | 4/1989 |
| EP | 0 484 483 B1 | 5/1991 |
| WO | WO 90/02581 | 3/1990 |

* cited by examiner

*Primary Examiner*—Chandrika Prasad

(57) ABSTRACT

A connector assembly for coupling an electrical lead to an electrically energized device includes a non-conductive housing member with an elongated bore. A block member in the bore proximate the sealed end has a coaxial through bore. A first of multiple side by side pairs of seal assemblies and contact assemblies in the bore is proximate the block member, a last one is nearest the bore entrance. Each contact assembly has electrical commonality with a terminal of the device. A strain relief zone fixed to the housing member in the bore engages the last seal assembly and faces the bore entrance. Force on the strain relief zone toward the block member firmly seals in the bore all components defining a central passage coaxial with the through bore enabling electrical contact among multiple lead terminals inserted into the bore, an associated contact assembly, and an associated terminal of the device.

22 Claims, 15 Drawing Sheets

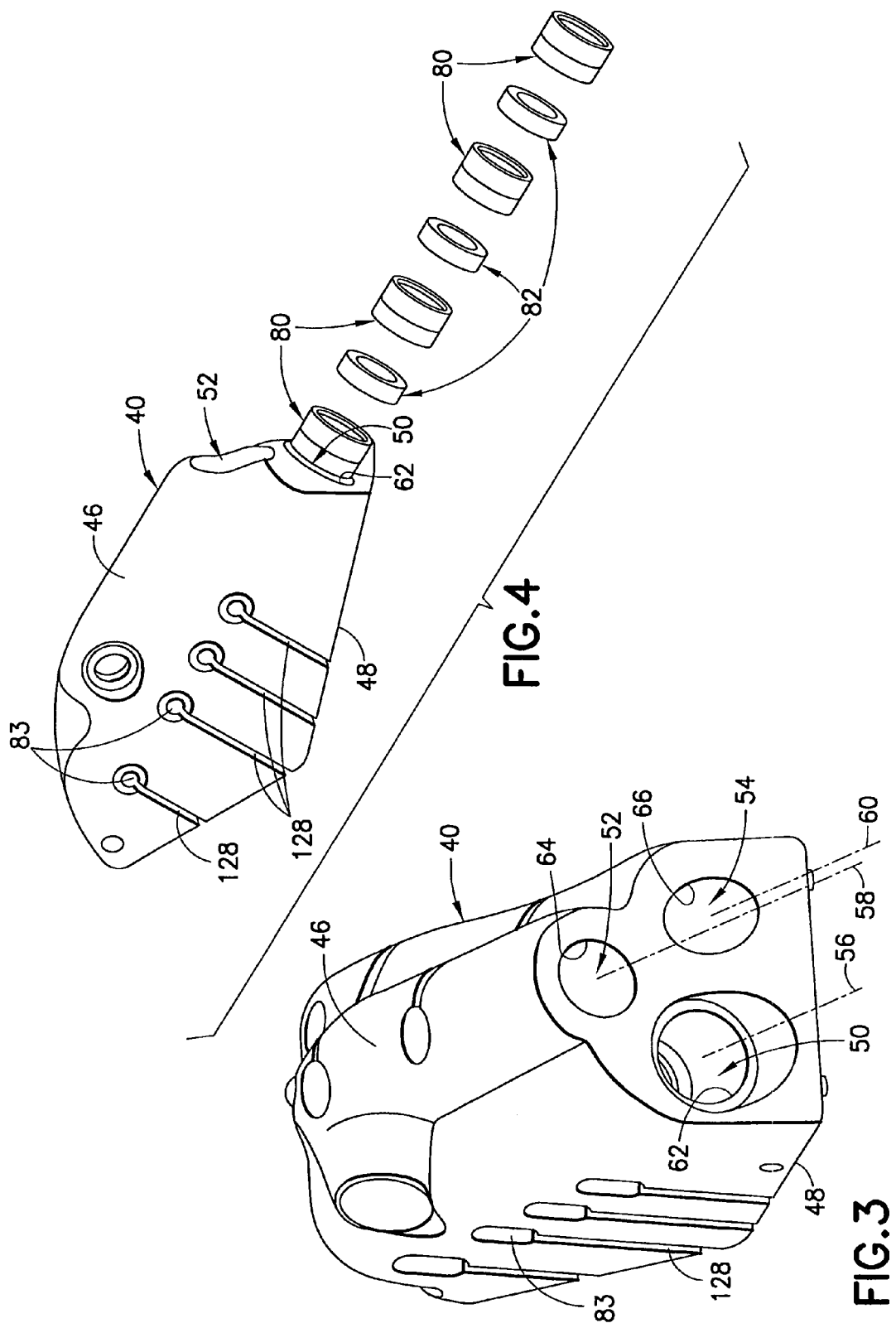

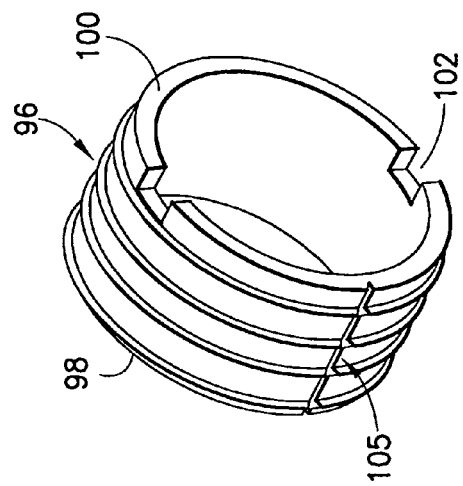
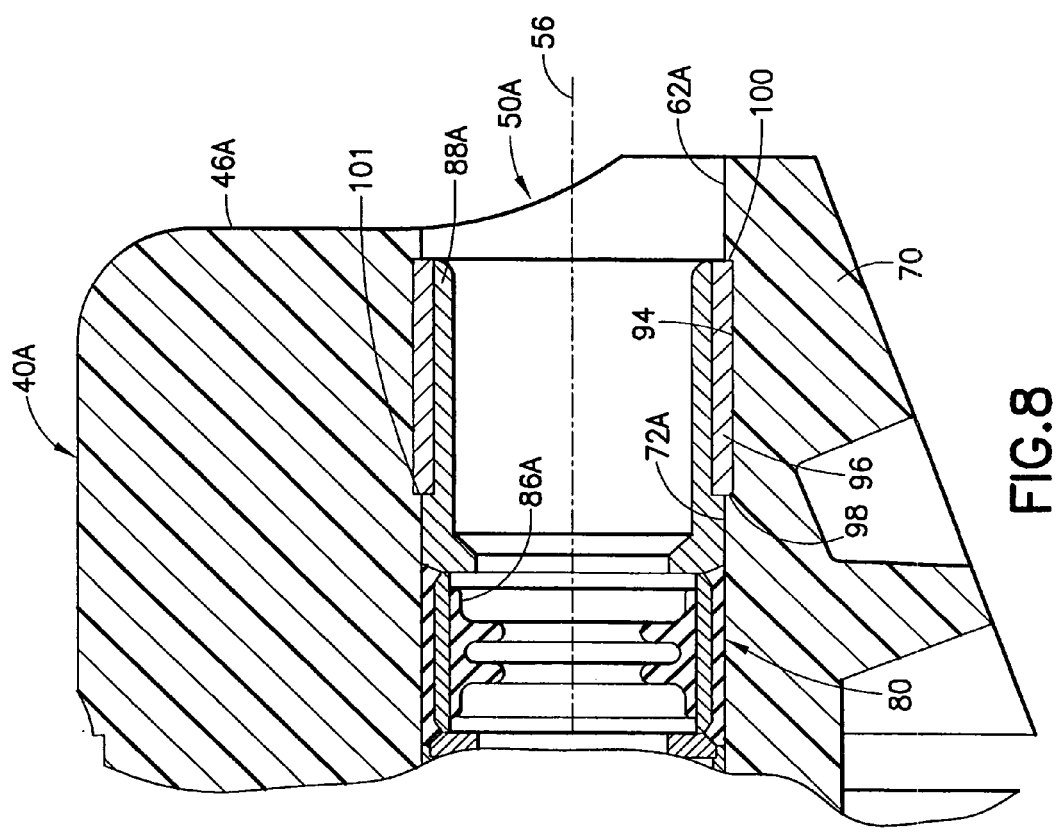

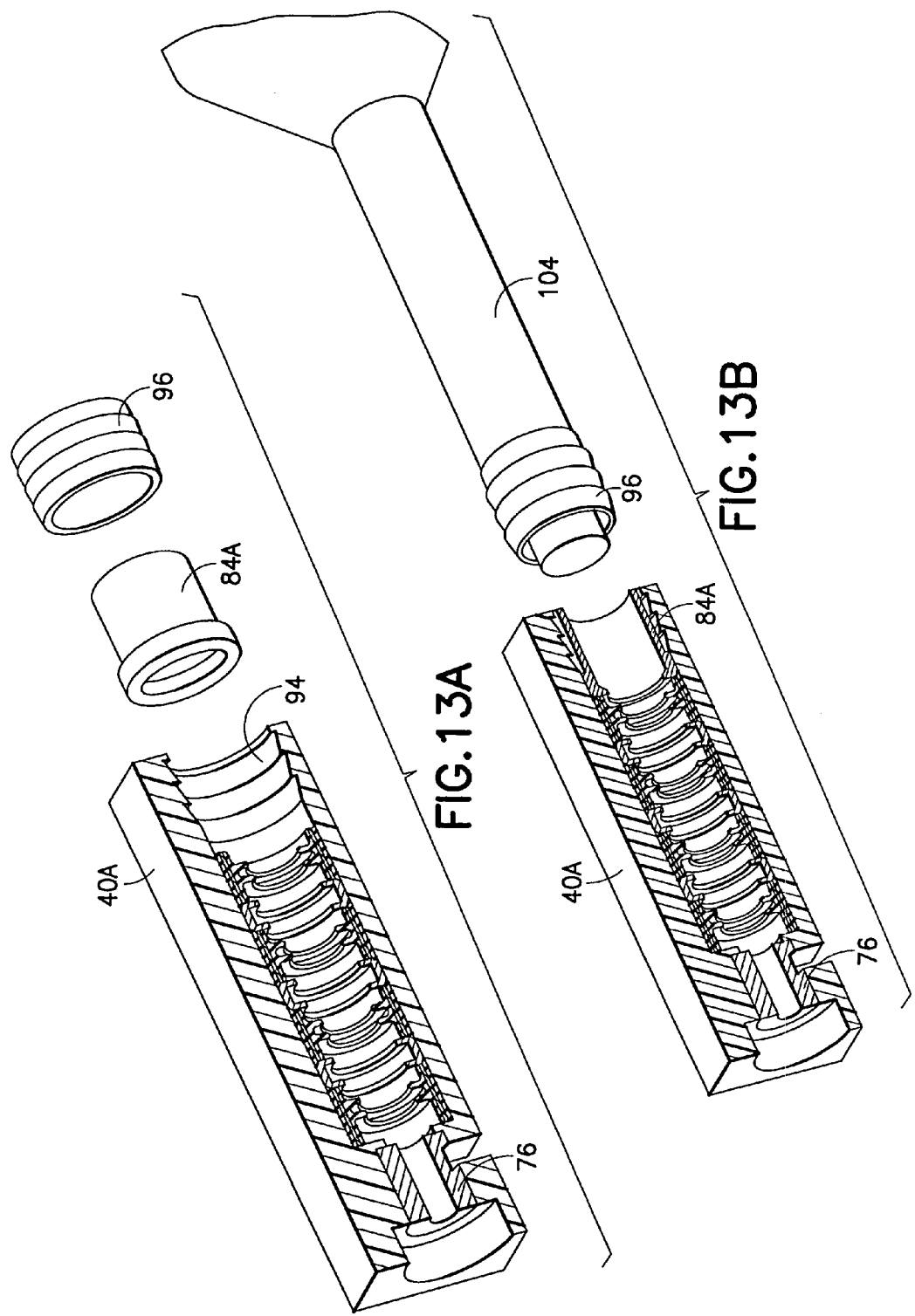

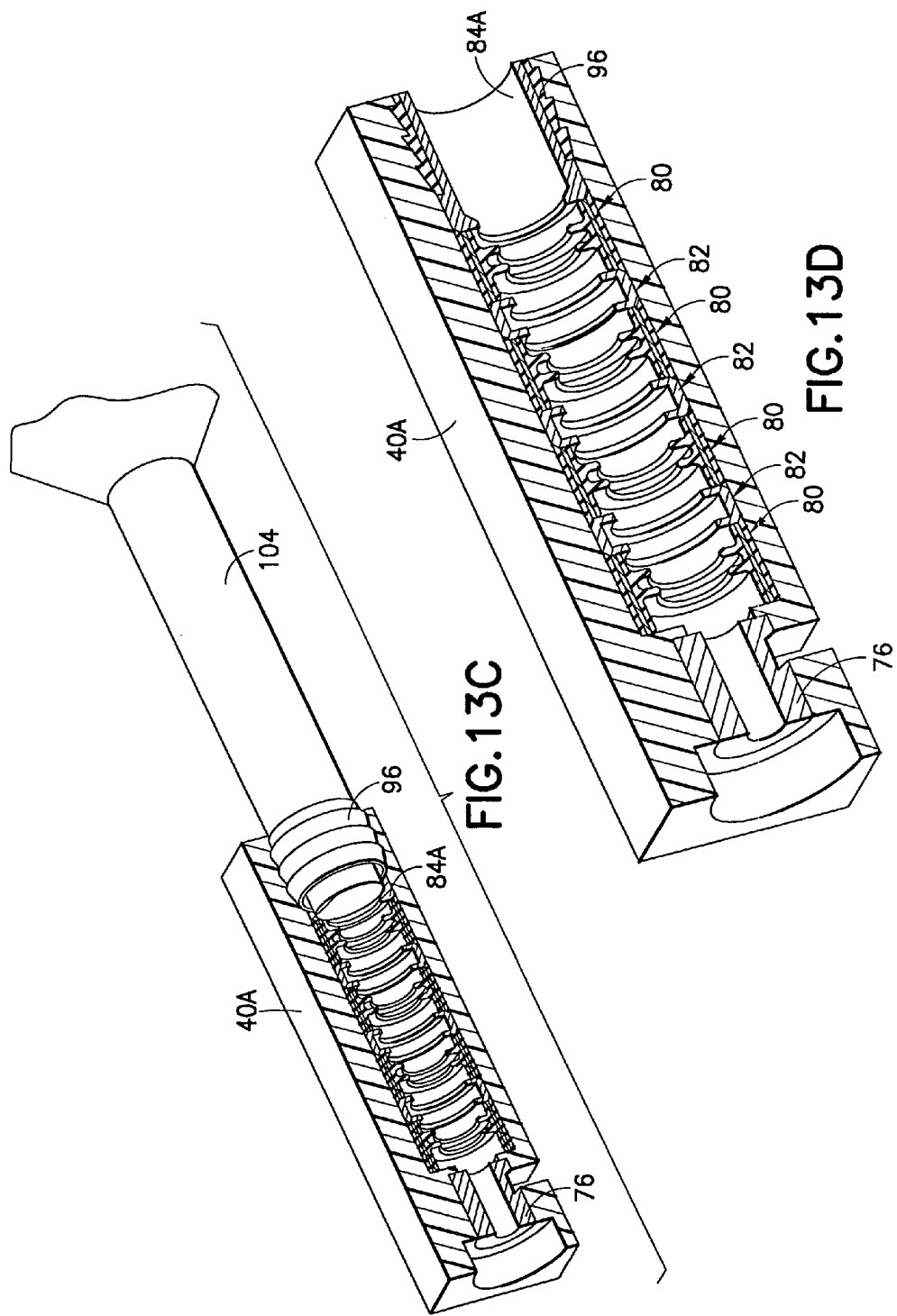

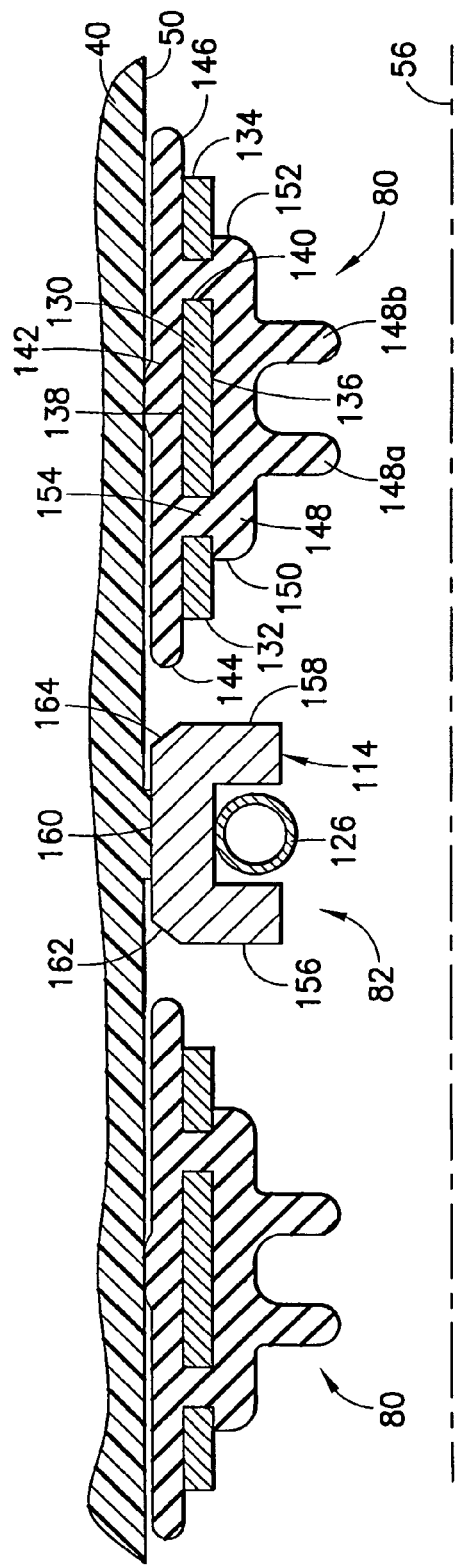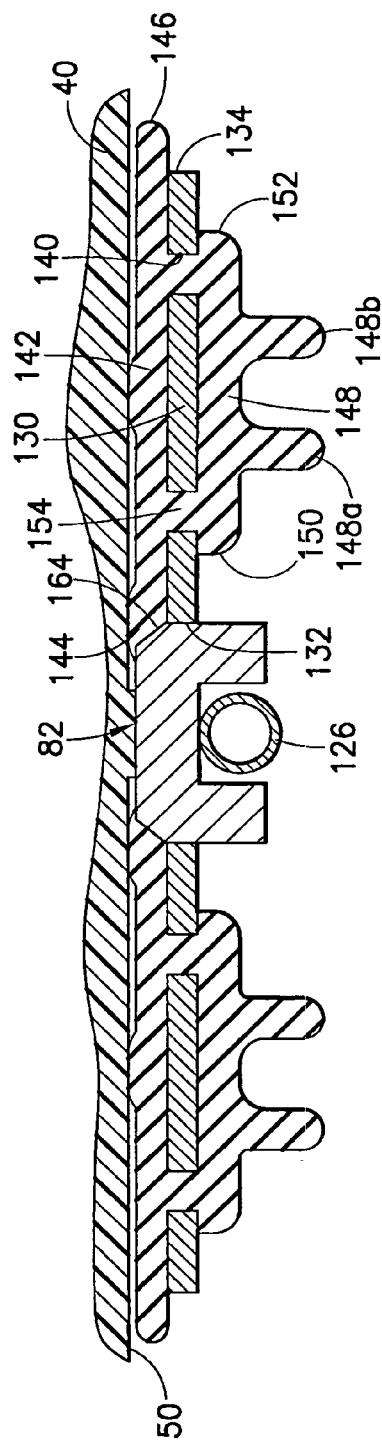
FIG.21
FIG.22

SYSTEM FOR LEAD RETENTION AND SEALING OF AN IMPLANTABLE MEDICAL DEVICE

FIELD OF THE INVENTION

The present invention relates generally to mechanisms for interconnecting electrical leads and electrical medical devices, and more particularly to systems and methods of interconnecting implantable electrical leads and implantable medical electrical devices such as pacemakers, implantable cardioverter-defibrillators (ICDs), and the like, which systems and methods enable a lead to be detachably, yet reliably, connected to the medical electrical device.

BACKGROUND

Cardiac stimulation systems commonly include a pulse generating device or pulse generator, such as a pacemaker or implantable cardioverter-defibrillator (ICD), that is electrically connected to the heart by at least one electrical lead. An electrical lead provides an electrical pathway between the pulse generator, connected to the proximal end of the lead, and myocardial tissue, in contact with the distal end of the lead. In such a manner, electrical pulses emitted by the pulse generator travel through the lead and stimulate the heart. Intrinsic cardiac signals may be sensed by electrodes located on the lead and conducted via the lead to sense amplifiers in the device for monitoring the heart's natural rhythm.

As implantable electrical devices have increased in their complexity, there have been an increasing variety of electrical lead systems developed for use in conjunction with these devices. Nowhere is this more apparent than in the context of ICDs, which may include two, three or more leads located for sensing or stimulating up to all four heart chambers. The leads themselves may carry one, two, three, or more electrodes, and may employ a variety of different electrical connector configurations and types. As a result, manufacturers of implantable pacemakers and ICDs have had to produce their products with a variety of connector block configurations, capable of use with different lead systems. However, there are standards which must be followed by manufacturers and the present invention is reflective of these standards.

The pulse generator is usually implanted in a subcutaneous cavity, and the leads extend either transvenously to the internal cavities of the heart, or to patch electrodes located on external surfaces of the heart.

The leads generally include at least one electrode located at a distal end and an electrical connector for interconnection to the pulse generator at the proximal end. The connector at the proximal end and the distal electrode are interconnected by at least one conductor extending through an insulated body. It is common, as already mentioned, for the leads to include two or more electrodes and two or more electrical contacts at the connector.

The connector is inserted into a receiving orifice in a header portion of the pulse generator. The header portion of the pulse generator defining the receiving orifice may be formed from an epoxy material which is formed and bonded to the main body of the pulse generator. The main body of the pulse generator is generally a metallic self-contained housing or can which encloses the source of electrical energy and electrical circuitry for controlling the electrical stimulus delivered by the lead.

Over the years, there have been a variety of connector designs in keeping with international design standards, for example, IS-1 for a 3.2 mm diameter lead connector and VS-1 for an earlier voluntary standard of the same size, each of which have no sealing rings but rely on seals provided on the leads themselves. Typical of such known designs are U.S. Pat. Nos. 5,012,807 and 5,413,595 to Stutz, Jr.

A relatively recent standard known as IS-4 (officially "Active implantable medical devices—four-pole connector system for implantable cardiac rhythm management devices") calls for seals to be placed in the connector cavity and not on the lead connector.

It was in light of the foregoing that the present invention was conceived and has now been reduced to practice.

SUMMARY

A connector assembly for coupling an electrical lead to an electrically energized device includes a non-conductive housing member with an elongated bore. A block member in the bore proximate the sealed end has a coaxial through bore. A first of multiple side by side pairs of seal assemblies and contact assemblies in the bore is proximate the block member and engaged with the base of the bore, a last one being located nearest the bore entrance. Each contact assembly has electrical commonality with a terminal of the device. A strain relief zone fixed to the housing member in the bore engages the last seal assembly and faces the bore entrance. Force on the strain relief zone toward the block member firmly seals in the bore all components defining a central passage coaxial with the through bore enabling electrical contact among multiple lead terminals inserted into the bore, an associated contact assembly, and an associated terminal of the device.

The present invention is in keeping with the earlier mentioned IS-4 (four-pole) lead connector standard which requires that seals be contained in the connector cavity and not on the lead connector. The present invention addresses the issues of:

(1) incorporating seals into a pre-molded header design,
(2) locating seals and electrical contacts in precise and repeatable axial locations,
(3) keeping seals and contacts concentric, that is, at precise radial locations,
(4) reducing the number of individual parts by using a novel method for creating a seals,
(5) eliminating the need for press-fits between components, and
(6) keeping the size of the connector cavity compact.

In earlier pre-molded header designs, seals were not required in the connector cavity because the lead connector contained sealing rings.

Three typical approaches for pre-molded header designs are: (1) press fitting components together and molding over press fit connector assemblies; (2) molding connector blocks and spring contacts into connector assemblies without seals and molding over connector assemblies; and (3) pressing connector blocks into openings in a pre-molded plastic header.

As to (1), press-fit designs or over-molded designs require enough axial length on seals and contacts for a press-fit shoulder between components to insure that over-molded material does not leak into the inside of the components. This construction may be practical when the connector comprises one or two electrical contacts and one or no seals. However, the IS-4 connector cavity has four seals and four electrical contacts with a center-to-center spacing of 0.089". A press-fit design for the IS-4 would require adding material to the components in both the radial and axial directions to create length and thickness for press fitting contact surfaces to seal surfaces.

As to (2), current T-Connector and DF-1 connectors of the assignee of the present invention do not contain seals. In the T-Connector design, the setscrew block and spring contact are molded together into one connector. The DF-1 connector block is typically molded directly into the header with a pin holding the connector block and presenting an opening for the lead.

As to (3), pressing connector blocks into openings in the pre-molded plastic header requires multiple connector block size openings in the pre-molded header and generally is not considered desirable for assembling sealing components into the header.

The IS-4 connector cavity requires four electrical contacts in the form of one setscrew block and three spring contacts as well as four seals. The key to the present invention is the seal design and the connector cavity assembly method. The connector cavity design of the invention suitable for the IS-4 connector includes a plastic header with a cylindrical bore opening. A first component insert molded into the header is a setscrew block or passive fixation block. Next, a seal is assembled into the bore by aligning the seal at the entrance of the bore and pushing the seal down the bore and against the base of the bore. Next, an electrical contact is pushed into the bore. Seals and electrical contacts are assembled in an alternating fashion into the bore. The final piece is a non-conductive rigid strain relief zone which serves to: (1) support the lead connector, (2) press the seals and electrical contacts together, and (3) lock the seals and electrical contacts within the bore.

The seals are created by injection molding silicone over a rigid seal housing, or over-molding. The seal housing contains multiple holes going through the perimeter. These holes are used to: (1) allow silicone to flow to the inside of the housing, and (2) to anchor the inner sealing rings to the housing. The purpose of using a housing is to have a rigid platform for the silicone sealing rings so that during assembly, the seals can be precisely located within the bore. The rigid seal housing and over-molded anchor design described above also holds the silicone seals into place during insertion and/or withdrawal of a lead connector.

One seal assembly contains two inner sealing rings and an outer sealing design. The outer seals are created when the final component, that is, the strain relief zone, is pressed into the bore, pressing seals against the electrical contacts. The seal housing ends press against the electrical contact ends creating a precise stacking, that is, with a hard edge to a hard edge. The two rings of silicone that extend past either side of the seal housing are pressed into the neighboring electrical contact's outer diameter. Silicone rings press against the plastic bore producing a seal against the bore, that is, the seal assembly outer diameter seal.

The axial pressure and electrical contact edge chamfer press the silicone rings out to the bore creating a radial seal between the outer diameter of the seal assembly and the bore. This outer diameter seal completes the electrical isolation between the electrical contacts.

As described, the invention allows for assembling the seals into the bore with very little interference between the seals and the bore, resulting in a substantially simplified assembly from earlier designs. The outer seal is produced in the last step of the assembly by pressing the last piece, that is, the strain relief zone, into the bore. The strain relief zone presses the seals and contacts against each other. Two methods of securing or compressing the components into place are: (1) using an arbor press and adhesive to press the strain relief zone into the bore; and (2) using a threaded compression sleeve to press and secure the strain relief zone into place.

It will be appreciated that while this invention is particularly applicable to the IS-4 (four-pole) lead connector standard, it can also be used to produce DF-1 and IS-1 connector cavities.

In short, this invention could be used on any device, medical and non-medical (pacemaker or ICD but not limited to these devices), where components need to be held in place in compression, possibly for a long period of time. The threaded retention sleeve along with the strain relief zone provide a reliable means of compressing components inside a bore. A primary application for this invention is on IS-4 connector bore assemblies as earlier related. Previously, for this purpose, it was necessary to use computer programming to code the force and displacement on a hydraulic push/pull machine. This was time consuming and required expensive machinery, fixtures to hold the assemblies, specialty pins to insert the strain relief zone, glue, fast assembling, and MTS machine know-how. In contrast, with the threaded retention sleeve of the invention, the assembly of the IS-4 bore has been drastically simplified.

In this easy and reworkable alternative to earlier constructions, a threaded sleeve is provided that can be turned down onto a shoulder added to the strain relief zone and into the connector bore retaining and compressing all of the components mechanically and reliably. The threaded sleeve retains all components inside the bore. It has external threads that match up to internal tapped threads in the bore (should optional self-tapping grooves be used, then these tapped threads are not necessary) and can be tightened and locked in place. The threaded retention sleeve rides against a shoulder added to the strain relief zone. As the threaded retention sleeve is tightened, it pushes the strain relief zone deeper into the bore and compresses the seals so the silicone is pushed against the inside of the bore making a good seal. This controlled compression ensures the proper placement of all the components for all other components that interact with the assembly. All that is needed, then, is to push all of the components into the bore, push in the strain relief zone, and turn in the threaded compression sleeve with a screwdriver-like tool.

A primary feature, then, of the present invention is the provision of a system for coupling a medical electrical lead to a medical device in a manner which satisfies current connector standards.

Another feature of the present invention is the provision of such a system which has the ability to incorporate a sealing component into a pre-molded header.

Yet another feature of the present invention is the provision of such a system with an over molded seal assembly design which increases ease of handling and ease of assembly of sealing components into the header.

A further feature of the present invention is the provision of such a system in which seals have a slip fit into bore for ease of assembly, seals between electrical contacts being produced in the last step of the assembly when the final piece presses seals and contacts against each other.

Yet another feature of the present invention is the provision of such a system in which a threaded compression sleeve is a reliable and convenient way to retain and compress components inside a bore, the degree of compression capable of being easily varied easily depending upon tolerance variation and design objectives.

Still a further feature of the present invention is the provision of such a system which requires no complicated machines or tools for assembly.

Another feature of the present invention is the provision of such a system which makes allowance for reworking the assembly in the event components are out of specification in contrast with a competitive glued approach with which one would not be able to salvage all of the proper components.

Yet another feature of the present invention is the provision of such a system which does not require skilled labor for fabrication.

Yet another feature of the present invention is the provision of such a system which does not entail a messy assembly process since no glue or adhesive is used.

Still another feature of the present invention is the provision of such a system which results in a reduced possibility of cracking the connector bore due to over-pressing during assembly.

Still a further feature of the present invention is the provision of such a system for which there is no time limit on how long it can take to put a bore together, compared with a competitive system using glue for which assembly must take place quickly with everything in place before the glue dries.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

BRIEF DESCRIPTION OF THE DRAWINGS

The foregoing aspects and other features of the present invention are explained in the following description, taken in connection with the accompanying drawings, wherein:

FIG. 3 is a perspective view of a connector assembly or header that is a component of the stimulating medical device of FIGS. 1 and 2;

FIG. 4 is an exploded perspective view of the stimulating medical device illustrated in FIG. 3 showing it with greater detail;

FIG. 8 is a detail cross section elevation view, similar to a portion of FIG. 5, of another embodiment of the connector assembly or header for the stimulating medical device;

FIG. 9 is a perspective view of a component illustrated in FIG. 8;

FIGS. 13A, 13B, 13C, and 13D are perspective views illustrating a series of successive steps in the assembly of one embodiment of the connector assembly or header according to the invention;

FIG. 21 is a detail cross section view illustrating a pair of seal assemblies and an intermediate contact assembly before they are fully assembled within the connector assembly or header; and FIG. 22 a detail cross section view similar to FIG. 21 illustrating the pair of seal assemblies and intermediate contact assembly when they are fully assembled within the connector assembly or header according to the invention.

DETAILED DESCRIPTION OF THE PREFERRED EMBODIMENTS

Figure 1:
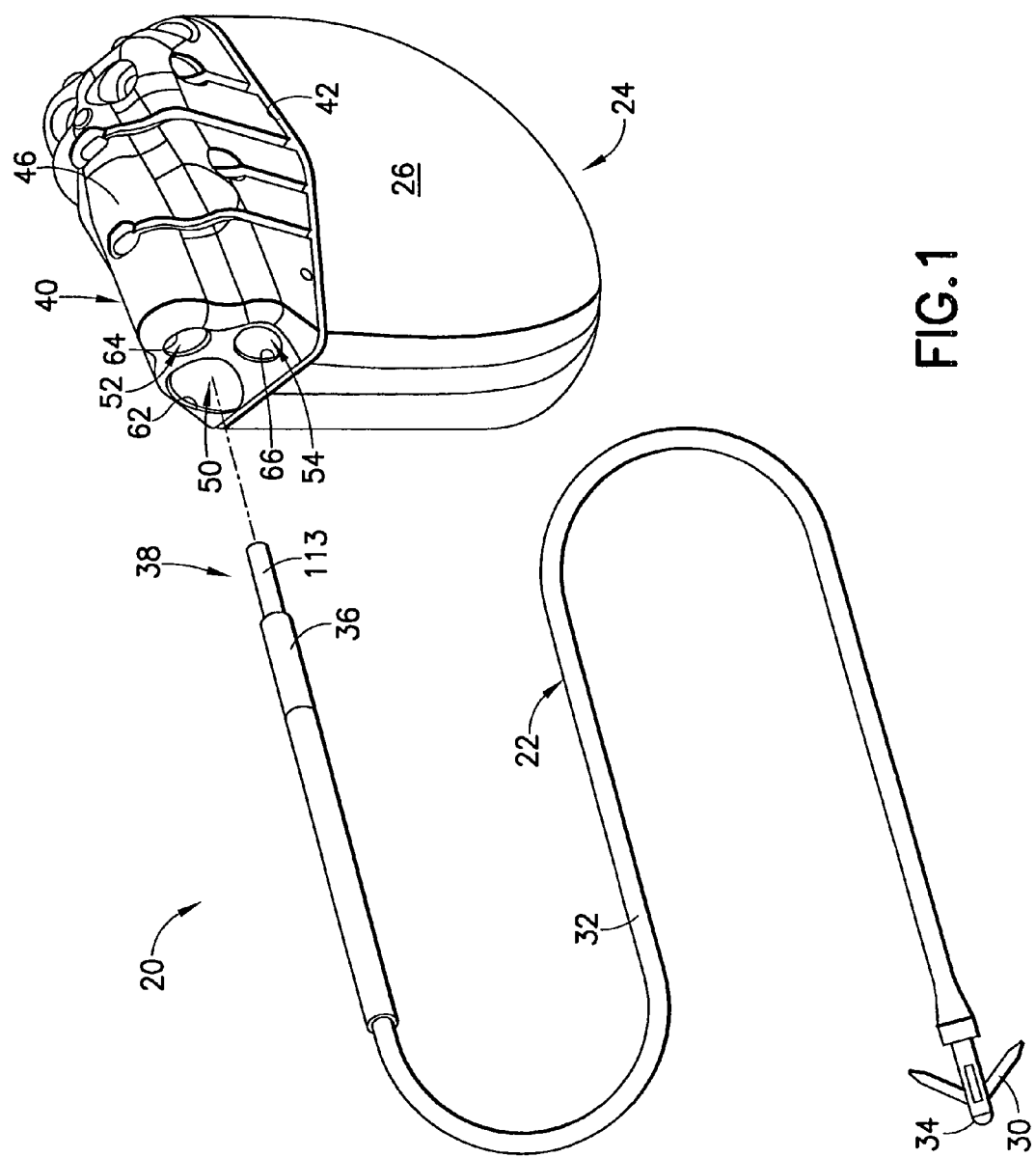
FIG. 1 is a perspective view illustrating of a system embodying the invention including an implantable lead in combination with a stimulating medical device or pulse generator such as a pacemaker.
Figure 2:
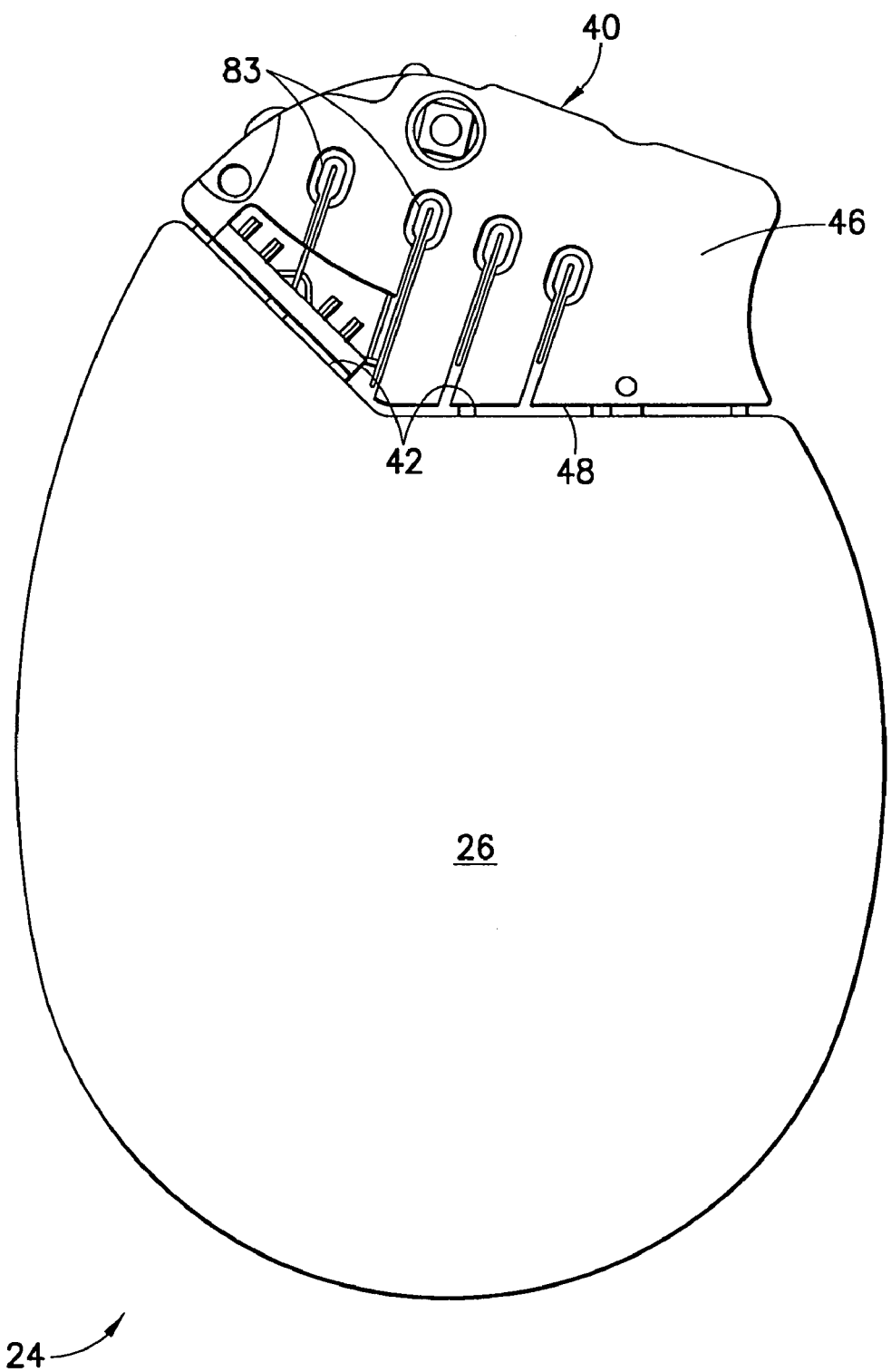
FIG. 2 is a side elevation view of the stimulating medical device of FIG. 1.

Refer now to the drawings and, initially, to FIG. 1 which illustrates a diagrammatic perspective view of a system 20 for coupling a body implantable medical electrical lead 22 to a medical device 24 including a sealed housing 26 containing a pulse generator for delivering electrical stimuli to body tissue. The lead 22 is of the endocardial type which may be attached to an interior wall of a heart by means of fixing tines 30, for example, which engage the tissue or trabeculae of the heart. The lead 22 also includes an insulating sheath 32 interconnecting a distal electrode 34 secured adjacent the interior wall of the heart, for example, and an electrical connector 36 at a proximal end 38 for attachment to the pulse generator 24, such as a pacemaker. The terms medical device, pulse generator, and pacemaker may be used interchangeably in this disclosure and the term pacemaker is not intended to be restrictive of the type of pulse generator to which the invention has application. Attachment to the pulse generator 24 is achieved via a connector assembly, or header, 40 incorporating features of the present invention. Although the present invention will be described with reference to the embodiments shown in the drawings, it should be understood that the present invention can be embodied in many alternate forms or embodiments. In addition, any suitable size, shape or type of elements or materials could be used.

As earlier noted, the present invention satisfies the IS-4 (four pole) lead connector standard requiring that that seals be contained in the connector cavity and not on the lead connector. Again, as earlier stated, but it bears repeating, both the lead 22 and, more importantly from the standpoint of the invention, the connector assembly 40, addresses the issues of:

(1) incorporating seals into a premolded header design;
(2) locating seals and electrical contacts in precise and repeatable axial locations;
(3) keeping seals and contacts concentric (precise radial locations);
(4) reducing the number of individual parts by using a novel method for creating a seals;
(5) eliminating the need for press-fits between components; and
(6) keeping the size of the connector cavity compact.

Figure 7:
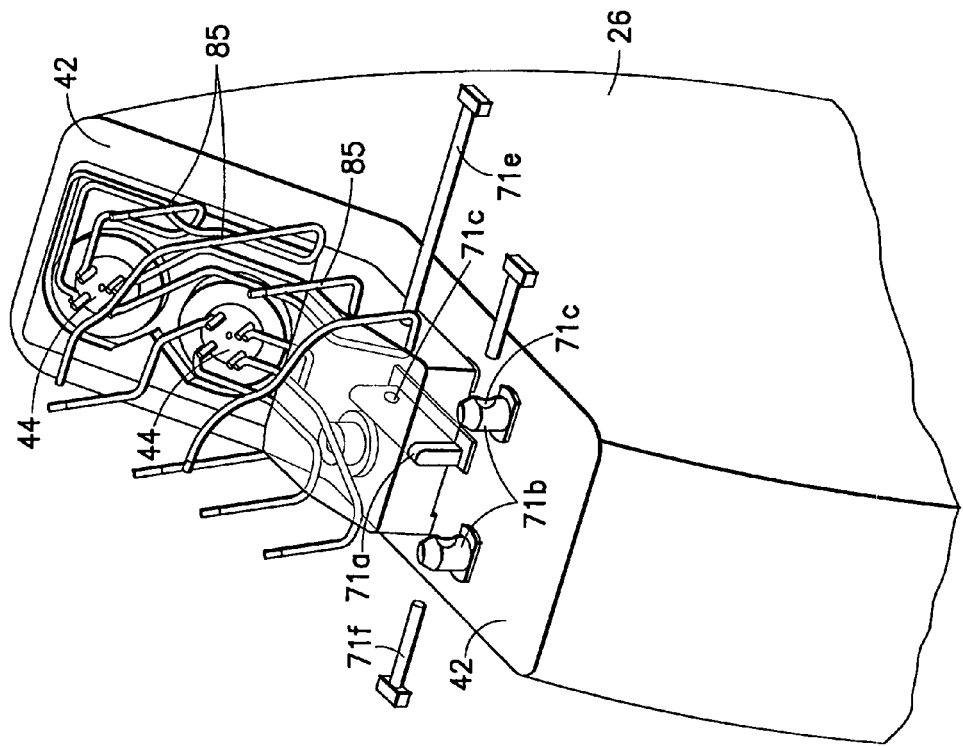
FIG. 7 is a perspective view of the uppermost portion of the housing of the medical device to which the connector assembly or header is to be attached.

Turning now to FIGS. 2–8 in addition to FIG. 1, the sealed housing 26 of the medical device is seen to have a mounting surface 42, best seen in FIG. 7, and a pair of electrically conductive feedthroughs 44 coupled to the pulse generator and projecting beyond the mounting surface. The header or connector assembly 40 is preferably pre-molded and necessarily of suitable non-conductive biocompatible thermoplastic material and is defined by an outer peripheral surface 46 and an undersurface 48 for mounting engagement on the mounting surface 42 of the medical device. The header 40, as illustrated, has a plurality of elongated cylindrical bores therein, 50, 52, and 54, respectively, having generally parallel longitudinal axes 56, 58, 60, and bore entrances 62, 64, 66, respectively. In this particular design, bore 50 is intended to receive an IS-4 lead through entrance 62 (as actually illustrated), bore 52 is intended to receive an IS-1 RA (right atrium) lead through entrance 64, and bore 54 is intended to receive an IS-1 LV (left ventricle) lead through entrance 66 (as actually illustrated).

Continued discussion of the construction of a bore will be limited to bore 50 for ease of explanation since bores 52 and 54 are of substantially similar design.

Figure 5:
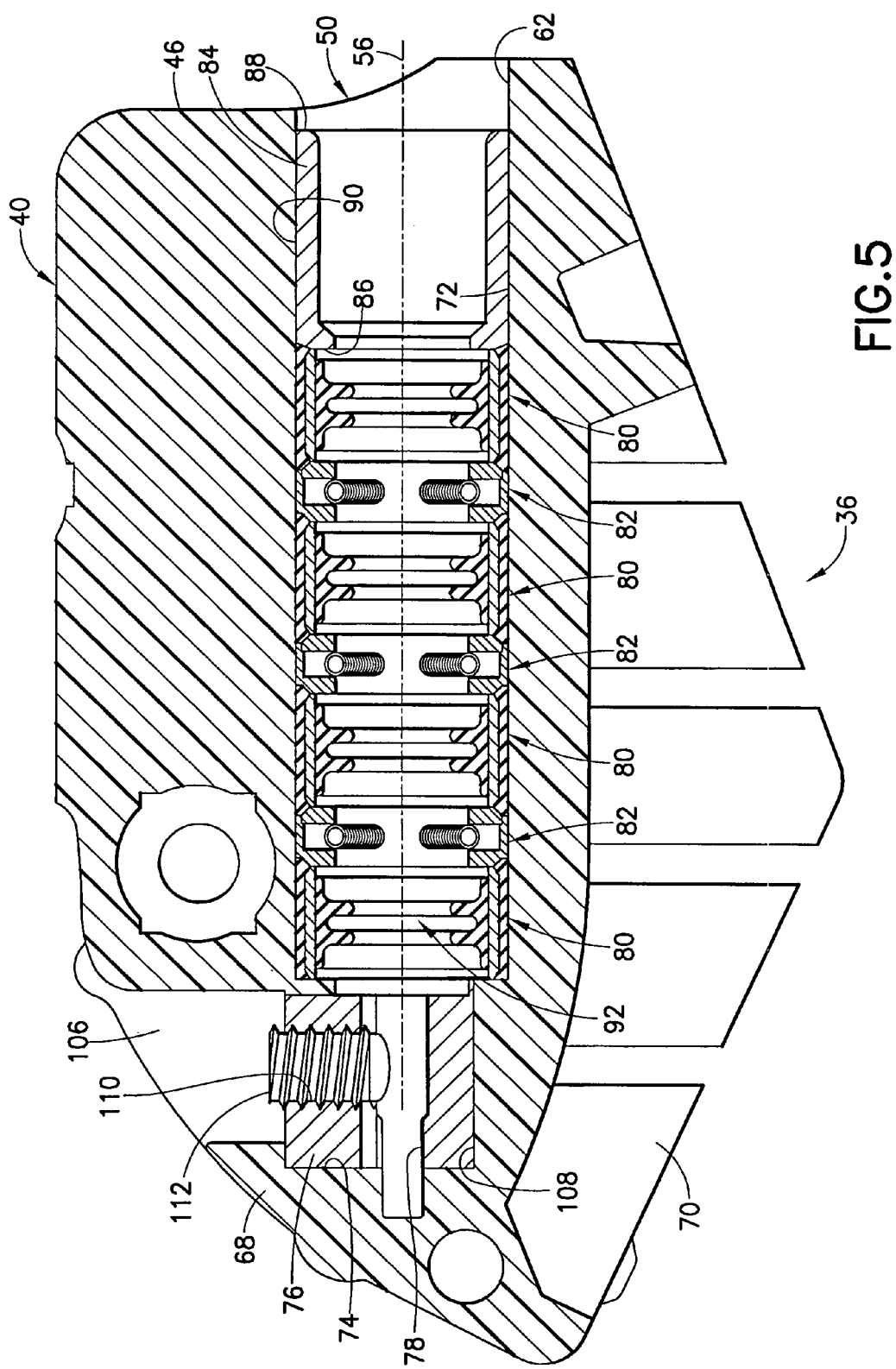
FIG. 5 is an cross section elevation view of the connector assembly or header for the stimulating medical device illustrated in FIGS. 1, 2, and 3.
Figure 6:
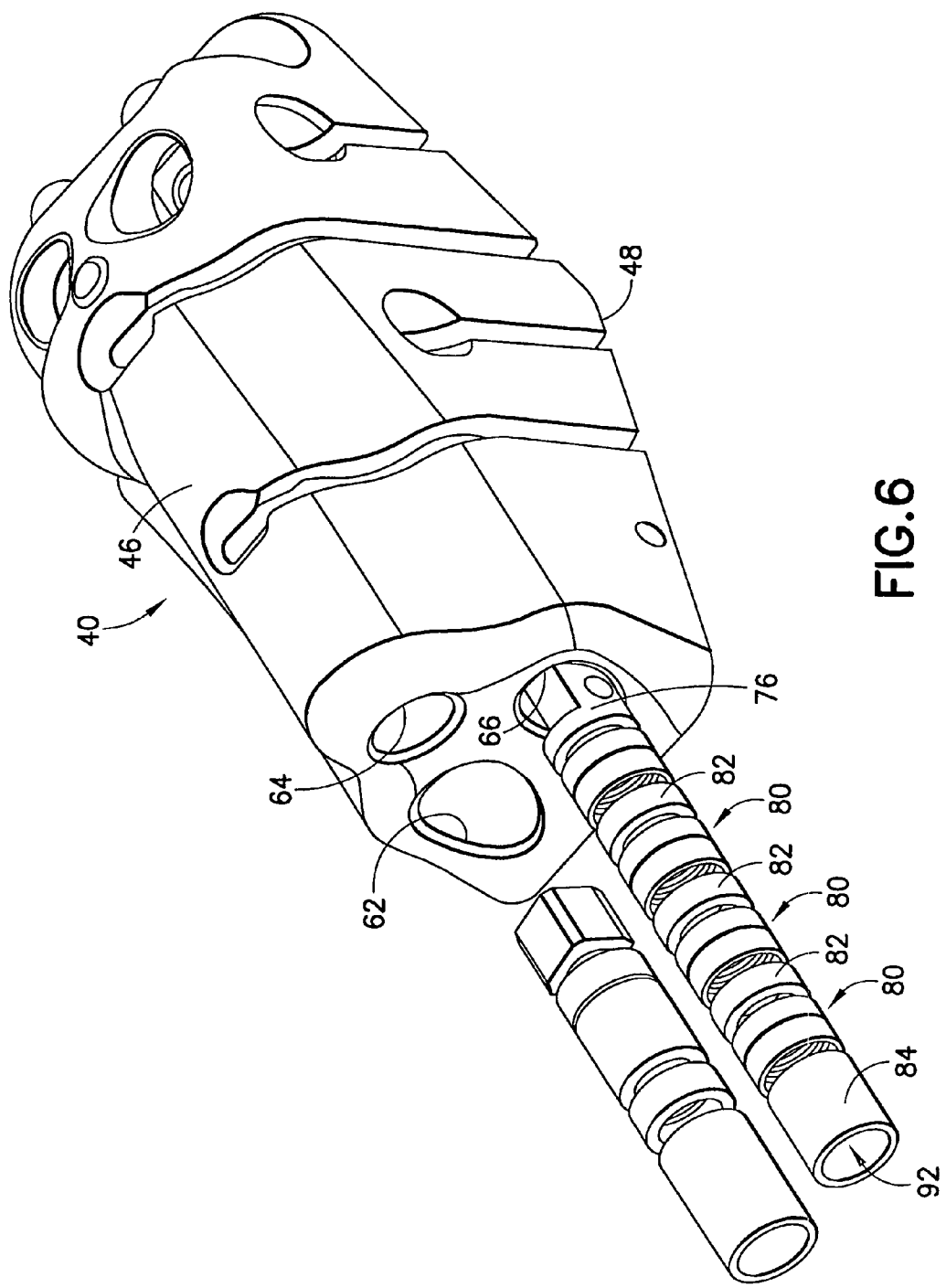
FIG. 6 is another exploded perspective view of the connector assembly or header for the stimulating medical device illustrated in FIG. 4 showing it receiving components for both IS-1 and IS-4 lead connector standards.

As best seen in FIG. 5, the header 40 includes a solid body portion 68 containing the cylindrical bores 50, 52, and 54 (see especially FIGS. 1 and 3) and a pair of opposed, generally parallel, skirt members 70 are integral with the solid body portion and extend away from the body portion to a lower rim which is the undersurface 48 for mounting engagement on the mounting surface 42 of the medical device. The cylindrical bore 50 has an inner peripheral surface 72 which extends between a terminal sealed end 74 and the bore entrance 62 at the outer peripheral surface 46.

Figure 7A:
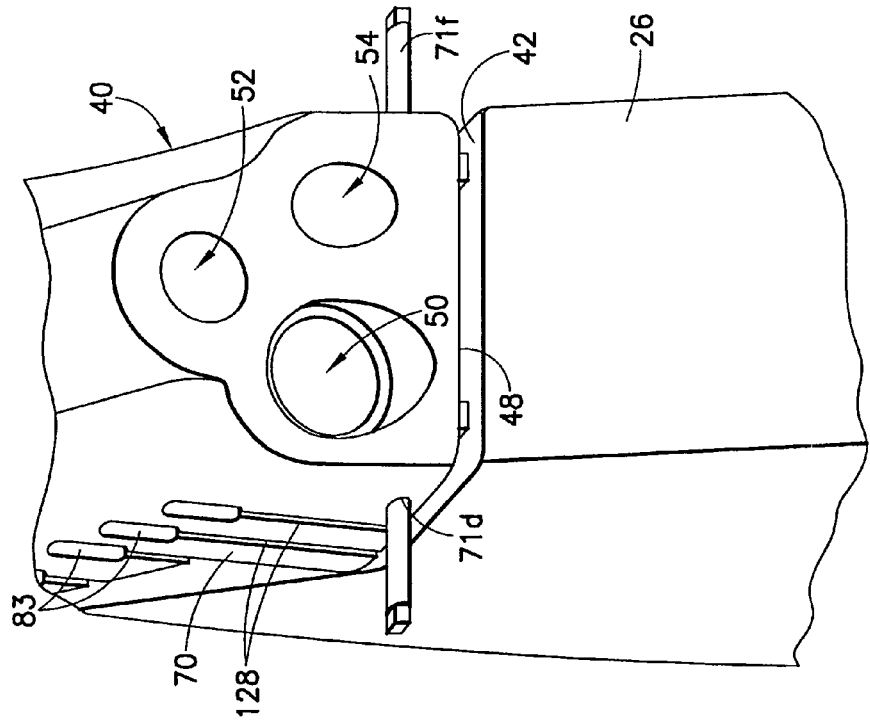
FIG. 7A is a perspective view of the uppermost portion of the housing of the medical device to which the connector assembly or header is actually attached.
Figures 10, 11:
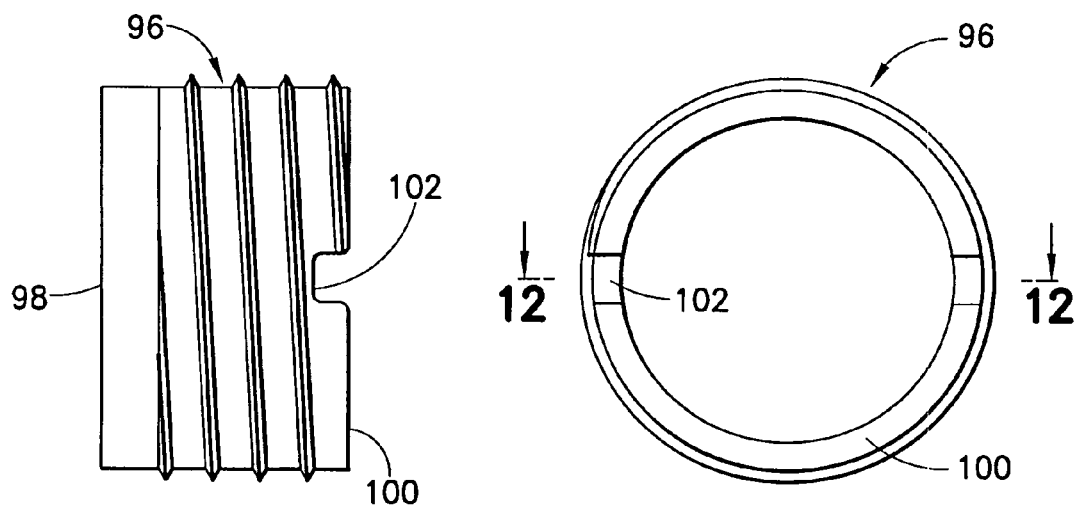
FIG. 10 is a side elevation view of the component illustrated in FIG. 9.
FIG. 11 is an end elevation view of the component illustrated in FIG. 9.
Figure 12:
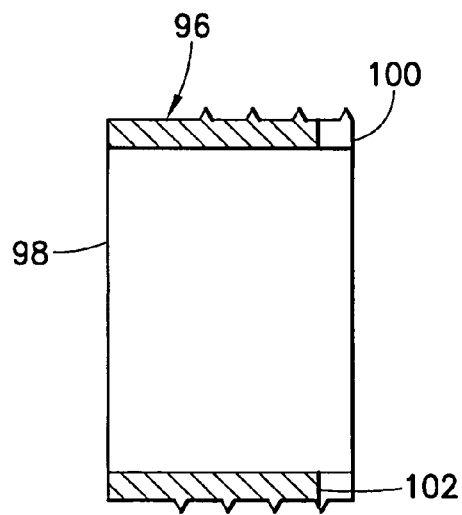
FIG. 12 is a cross section view taken generally along line 12—12 in FIG. 11.

The header 40 may be attached to the housing using any of a number of satisfactory constructions. One acceptable attachment construction is illustrated in FIGS. 7 and 7A. For this purpose, a stanchion 71a and a pair of posts 71b are provided integral with and projecting upward from the mounting surface 42. Mating holes 71c, 71d are formed in the stanchion 71a and in the skirt members 70, respectively, to receive a mounting pin 71e and similarly in the posts 71b and in the skirt members to receive mounting pins 71f. Thereafter, the mounting pins 71e and 71f are suitably moved to fully fastened positions and secured with the under surface 48 congruent with the mounting surface 42.

A setscrew block 76 is insert molded into the header and positioned coaxially to the cylindrical bore 50 of the header 40 proximate the terminal sealed end 74 and itself has a through bore 78 coaxial with the cylindrical bore 50. A plurality of pairs of seal assemblies 80 and contact assemblies 82 are positioned, sequentially, in side by side relationship, in the cylindrical bore 50, a first one of the seal assemblies being proximate the setscrew block, a last one of the seal assemblies being nearest the bore entrance 62. Additionally, the header 40 has an aperture 83 extending between the outer peripheral surface 46 and the inner peripheral surface 72 aligned with each contact assembly 82 and a conductor wire 85 (FIG. 7) electrically connects a feedthrough 44 and each contact assembly 82 enabling electrical contact to be made between each contact assembly and an associated terminal on the electrical lead 22 inserted through the bore entrance 62 into the cylindrical bore 50 of the header 40. The actual manner of electrical connection will be described below. Thus, each contact assembly 82 has electrical commonality with an associated electrically conductive feedthrough 44 carried by the sealed housing 26 of the medical device, coupled to a pulse generator within the sealed housing, the conductor wire 85 projecting from the medical device.

A strain relief zone 84 is also positioned in the cylindrical bore 50 and fixed to the header to provide strain relief to the lead connector 36 that is inserted into the header bore. The strain relief zone 84 includes an annular shoulder 86 engaged with the last one of the seal assemblies 80 and an annular rim 88 spaced from the annular shoulder and facing the bore entrance 62 such that with force applied on the annular rim along the longitudinal axis 56 toward the setscrew block 76, the plurality of pairs of seal assemblies 80 and contact assemblies 82 and the strain relief zone 84 become firmly, sealingly, held between the proximal annular surface and the terminal sealed end. Then, in one embodiment, as illustrated in FIG. 5, for permanency of the sealing engagement, suitable adhesive is applied, then cured, at interface 90 between the strain relief zone and the inner peripheral surface 72 of the header bore 50 thereby affixing the strain relief zone to the header.

The plurality of pairs of seal assemblies 80 and contact assemblies 82 and the strain relief zone 84 together define a central passage 92 (FIGS. 5 and 6) coaxial with the through bore 78 of the setscrew block 76 and extending between the setscrew block and the bore entrance 62. With this construction, electrical contact is made between each contact assembly 82 and an associated terminal on the electrical lead 22 inserted through the bore entrance 62 into the cylindrical bore 72 of the header 40.

Alternatively, a modified strain relief zone 84A may be provided as illustrated in FIGS. 8–13D. For describing the modified strain relief zone 84A, the suffix "A" will be applied to all components which are directly associated with the strain relief zone 84 and which have been modified in this instance. For the strain relief zone 84A, an inner peripheral surface 72A of a cylindrical bore 50A of a header 40A has a tapped surface 94 adjacent the bore entrance 62A. An externally threaded annular compression sleeve 96 is slidably received on and coaxial with the strain relief zone 84A which has been counter bored and threadedly engaged with the tapped inner peripheral surface 94 of the elongated cylindrical bore 50A adjacent the bore entrance 62A. The compression sleeve 96 extends between a proximal annular surface 98 and a distal annular surface 100, the proximal annular surface engaged with a distally facing annular shoulder 101 of the counter bored strain relief zone 84A. By reason of this construction, with rotation of the compression sleeve in one direction about the longitudinal axis 56, the seal assemblies 80, the contact assemblies 82, and the strain relief zone 84A become firmly held between the proximal annular surface 98 and the terminal sealed end 74.

As seen especially well in FIGS. 9–12, the distal annular surface 100 of the annular compression sleeve 96 has a pair of diametrically opposed tool features 102 for reception of a suitable tool 104 (FIGS. 13B, 13C) for threadedly advancing (see FIGS. 13A–13D) the compression sleeve until the plurality of pairs of seal assemblies 80, contact assemblies 82, and the strain relief zone 84A are all firmly mutually engaged. With this design, there is no concern with problems of applying adhesive, curing the adhesive, and cleaning up afterwards, namely, all of the challenges associated with the construction of the earlier-described strain relief zone 84.

It will also be appreciated that in the instance of the strain relief zone 84A, the inner peripheral surface of the bore 50A may be smooth initially and tapped by means of the compression sleeve 96. Specifically, this result would be achieved with the use of self-tapping grooves 105 (FIG. 9) which may optionally be provided on the threaded peripheral surface of the compression sleeve 96.

Turn back now to FIG. 5 for a continuing description of the setscrew block 76. It should be noted that the header 40 has a transverse bore 106 extending between the outer peripheral surface 46 and the setscrew block 76. Also, the setscrew block 76 has a tapped bore 110 coaxial with the transverse bore 106. A setscrew 112 receivable through the transverse bore 106 and threadedly engaged with the tapped bore 110 serves to mechanically and electrically engage a pin tip 113 of the lead 22. The setscrew block 76 is insert molded into the header so that bore 78 is coaxial with 56.

Figure 15:
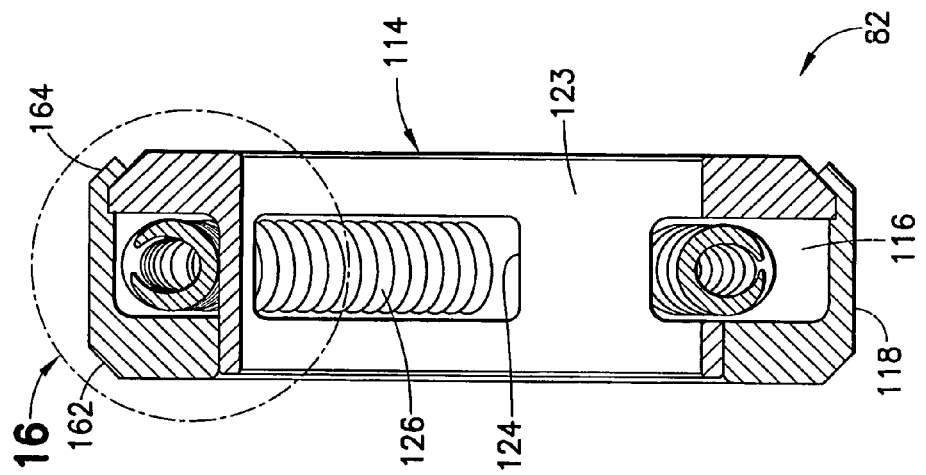
FIG. 15 is a cross section view taken generally along line 15—15 in FIG. 14.
Figure 14:
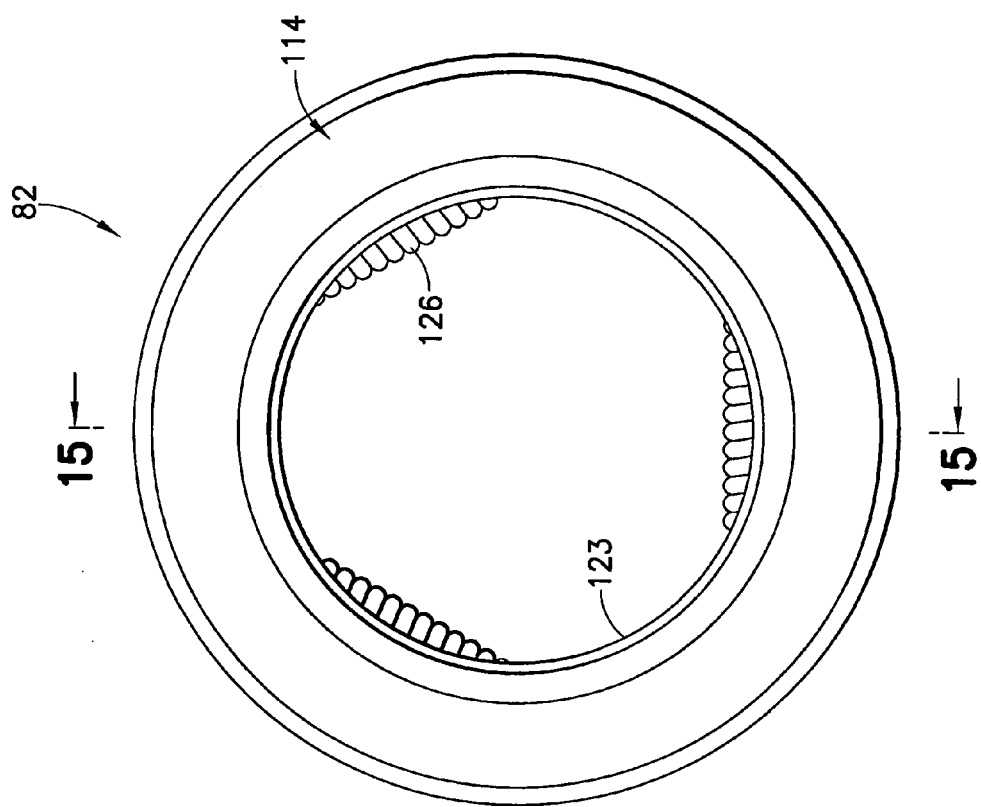
FIG. 14 is an end elevation view of a contact assembly according to the invention.
Figure 16:
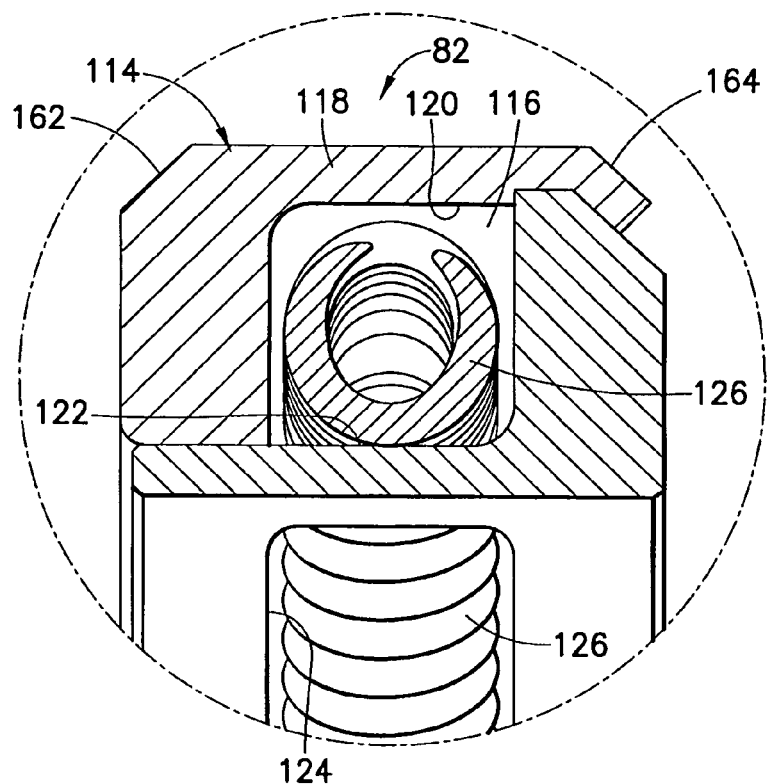
FIG. 16 is a detail cross section view illustrating a portion of FIG. 16 in greater detail.
Figure 17:
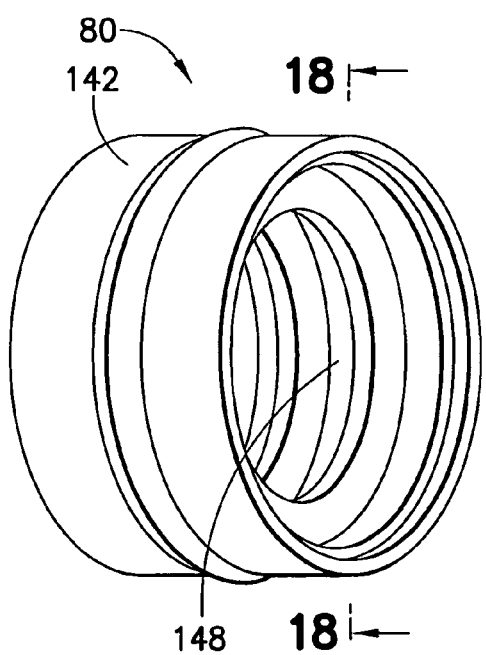
FIG. 17 is a perspective view of a seal assembly according to the invention.
Figure 18:
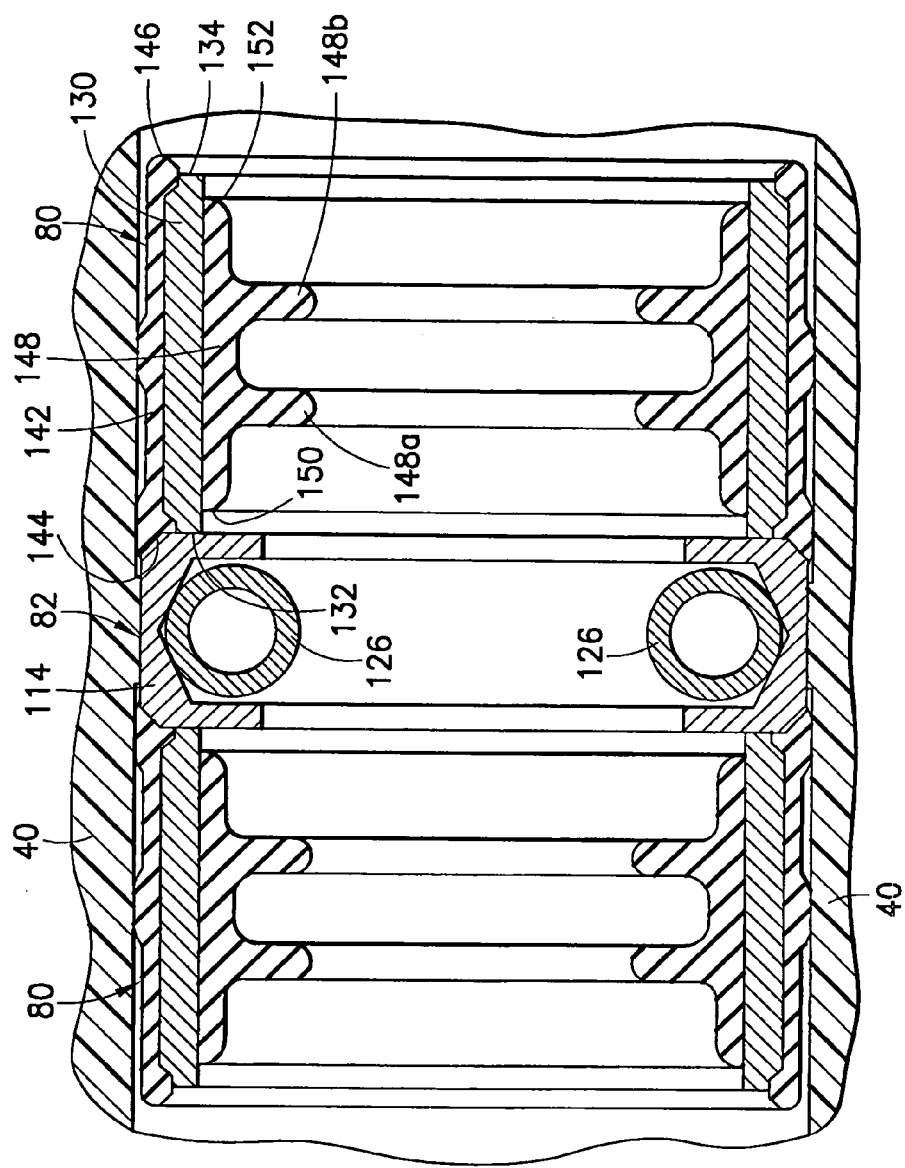
FIG. 18 is a cross section view taken generally along line 18—18 in FIG. 17.
Figure 19:
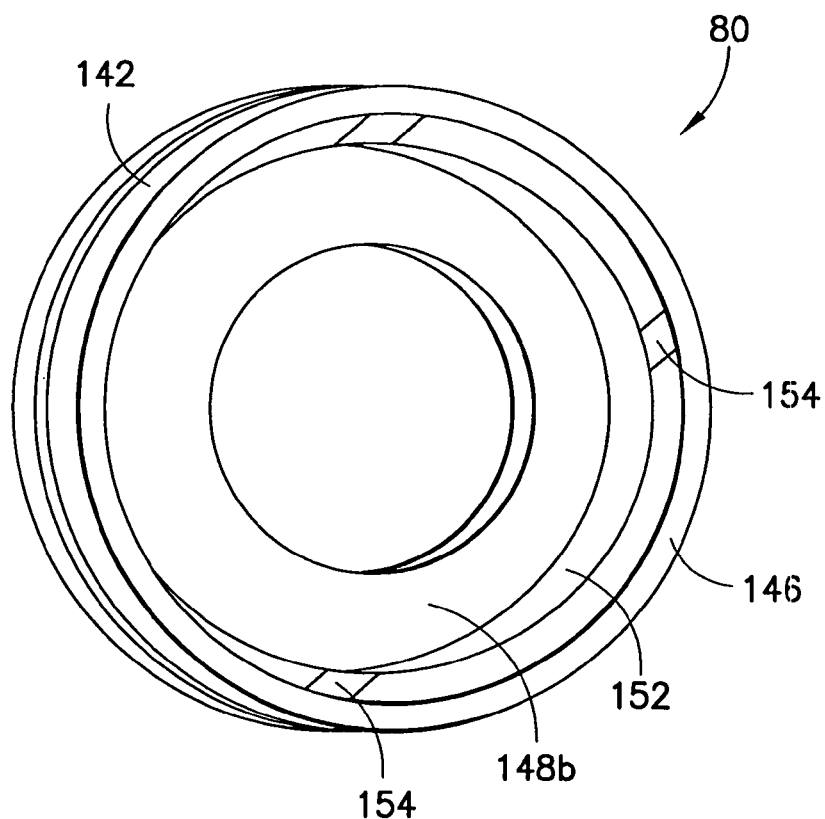
FIG. 19 is a slight perspective view, shown primarily from an end, of the seal assembly illustrated in FIGS. 17 and 18.
Figure 20:
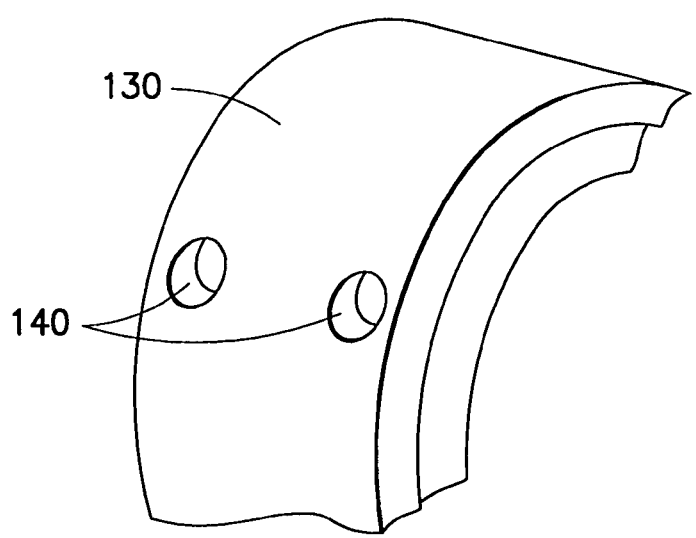
FIG. 20 is a detail perspective view of a component of the seal assembly illustrated in FIGS. 17–19.

With continuing reference to FIG. 5, turn now also to FIGS. 14, 15, and 16 for a description of each contact assembly 82. Each contact assembly 82 includes an annular housing 114 defining an interior space 116, the housing including a tubular wall 118 having an outer surface 120 facing the interior space 116 and an inner surface 122 defining a central opening 123 adapted to receive an electrical contact. The tubular wall defines at least one aperture 124 being a slot extending circumferentially along the wall of the housing. Indeed, there may be a plurality of such circumferentially spaced-apart slots, three for example, and they may be of equal length and equiangularly spaced apart. A garter spring 126 contained within the interior space 116 of the housing 114 has an inner diameter and encircles the outer surface 120 of the wall 118 under preload so that a portion of the inner diameter of the spring projects through the aperture 124 into the central opening 123 of the housing for engaging an electrical contact 36 received within the central opening.

Viewing, now, especially FIG. 4, the header 40 is seen to have a plurality of spaced, generally parallel, channels 128 in its outer peripheral surface 46 extending from each aperture 83 toward the under surface 48 and toward the mounting surface 42 of the housing 26. Each channel 128 extends not only on the solid body portion 68 (FIG. 5) but also along the skirt members 70 to the extremity of the under surface 48. Each conductor wire 85 (FIG. 7) is received in each associated channel 128 and extends to an associated aperture 83 at which it engages a contact assembly 82 aligned with that particular aperture thereby completing electrical continuity between the contact assembly, an associated conductive feedthrough 44, and the pulse generator contained in the housing 26.

Turn now especially to FIG. 5 for the overview and to FIGS. 17–22 for the specifics of the construction of each seal assembly 80. As seen especially well in FIGS. 18, 21, and 22, each seal assembly 80 includes a cylindrical seal housing 130 extending between opposed rims 132, 134. The seal housing 130 has an inner surface 136 and an outer surface 138 and a plurality of through holes 140 extending between the inner surface and the outer surface. The seal housing is composed of suitable non-conductive material and is preferably a rigid cylinder of uniform thickness and width. An outer seal 142 overlies the outer surface 138 and has proximal and distal lips 144, 146 which extend, respectively, beyond the opposed rims 132, 134 of the seal housing 130. An inner seal 148 overlies the inner surface 136 and extends to opposed edges 150, 152 spaced inwardly from the opposed rims 132, 134, respectively, of the seal housing 130. The inner seal also has a pair of spaced inwardly projecting uniformly dimensioned sealing rings 148a and 148b for firmly and sealingly gripping the proximal end 38 of the lead 22 when introduced into the bore 50 of the header 40 and, more specifically, into the central passage 92. A plurality of anchor members 154 are received in the through holes 140 integral with the outer seal 142 and with the inner seal 148 for fixedly attaching the outer seal and the inner seal to the seal housing. The outer seal, inner seal, and anchor members are composed of a suitable biocompatible material, silicone being preferable and molded onto the seal housing in a known manner.

Before describing the manner of sealing achieved by the invention, it is first necessary to provide additional description of each contact assembly 82. Continuing to view FIGS. 18, 21, and 22, it will be seen that the annular housing 114 of each contact assembly 82 has axially spaced proximal and distal sidewalls 156, 158, respectively, a terminal rim 160, a first chamfered edge 162 intermediate the proximal sidewall 156 and the terminal rim 160, and a second chamfered edge 164 intermediate the distal sidewall 158 and the terminal rim.

With this construction, upon rotation of the compression sleeve 96 about the longitudinal axis 56, and proceeding from viewing FIG. 21 to viewing FIG. 22, and continuing to view FIG. 5, a proximal lip 144 of the outer seal 142 nearest the setscrew block 76 deformably engages and bottoms out on the bottom of the bore 50. The annular shoulder of the strain relief zone 84 deformably engages a distal lip 146 of the outer seal 142 proximate the strain relief zone and, for each of the plurality of pairs of seal assemblies 80 and contact assemblies 82, a proximal rim 132 of the seal housing 130 engages a distal sidewall 158 of the annular housing 114 of the contact assembly 82 and a proximal lip 144 of the outer seal 142 deformably engages the second chamfered edge 164 of the annular housing of the contact assembly, and a distal lip 146 of the outer seal 142 deformably engages the first chamfered edge 162 of the annular housing 114 of the contact assembly 82.

With this description now finalized, the goals earlier announced, namely, to:

incorporate seals into a premolded header design, locate seals and electrical contacts in precise and repeatable axial locations, keep seals and contacts concentric with precise radial locations, reduce the number of individual parts by using a novel method for creating a seals, eliminate the need for press-fits between components, and keep the size of the connector cavity compact have all been achieved.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. A system for coupling a medical electrical lead to a medical device comprising:
 a header of non-conductive material having an outer peripheral surface, an undersurface for mounting engagement on the medical device, an elongated cylindrical bore therein having a longitudinal axis and an inner peripheral surface extending between a terminal sealed end and a bore entrance at the outer peripheral surface;
 a setscrew block insert molded into the header and positioned coaxially to the cylindrical bore of the header proximate the terminal sealed end and having a through bore coaxial with the cylindrical bore of the header;
 a plurality of pairs of seal assemblies and contact assemblies positioned, sequentially, in side by side relationship, in the cylindrical bore of the header, a first one of the seal assemblies being proximate the setscrew block, a last one of the seal assemblies being nearest the bore entrance, each contact assembly having electrical commonality with an electrically conductive feedthrough carried by a sealed housing of the medical device and coupled to a pulse generator within the sealed housing and projecting from the medical device; and
 a strain relief zone positioned in the cylindrical bore of the header and fixed thereto and including an annular shoulder engaged with the last one of the seal assemblies and an annular rim spaced from the annular shoulder and facing the bore entrance such that with force applied on the annular rim of the strain relief zone along the longitudinal axis toward the setscrew block, the plurality of pairs of seal assemblies and contact assemblies and the strain relief zone become firmly, sealingly, held between the proximal annular surface and the terminal sealed end, then with adhesive applied between the strain relief zone and the header bore permanently affixing the strain relief zone to the header, the plurality of pairs of seal assemblies and contact assemblies and the strain relief zone together defining a central passage coaxial with the through bore of the setscrew block and extending between the setscrew block and the bore entrance;
 whereby electrical contact is made between each contact assembly and an associated terminal on the electrical lead inserted through the bore entrance into the cylindrical bore of the header.

2. A system as set forth in claim 1 wherein the header is premolded of biocompatible electrically non-conductive material.

3. A system as set forth in claim 1 wherein with adhesive applied between the strain relief zone and the header bore, the strain relief zone is permanently affixed to the header.

4. A system as set forth in claim 1
 wherein the premolded header has a transverse bore extending between the outer peripheral surface and the setscrew block;
 wherein the setscrew block has a tapped bore coaxial with the transverse bore; and
 including:
 a setscrew receivable through the transverse bore and threadedly engaged with the tapped bore for fixedly engaging a pin tip of the electrical lead.

5. A system as set forth in claim 1
 wherein the inner peripheral surface of the cylindrical bore has a tapped surface adjacent the bore entrance; and
 including:
 an externally threaded annular compression sleeve slidably received on and coaxial with the strain relief zone and threadedly engaged with the inner peripheral surface of the elongated cylindrical bore adjacent the bore entrance, the compression sleeve extending between a proximal annular surface and a distal annular surface, the proximal annular surface engaged with the annular shoulder of the strain relief zone, such that with rotation of the compression sleeve in one direction about the longitudinal axis, the pair of seal assemblies, the contact assembly, and the strain relief zone become firmly held between the proximal annular surface and the terminal sealed end.

6. A system as set forth in claim 5 wherein the distal annular surface of the annular compression sleeve has a pair of tool features for reception of a tool for threadedly advancing the compression sleeve until the plurality of pairs of seal assemblies and contact assemblies, and the strain relief zone are all firmly mutually engaged.

7. A system as set forth in claim 1
 wherein each seal assembly includes:
 a cylindrical seal housing extending between opposed rims and having an inner surface and an outer surface and a plurality of through holes extending between the inner surface and the outer surface;
 an outer seal overlying the outer surface and extending beyond the opposed rims of the seal housing;
 an inner seal overlying the inner surface and extending to opposed edges spaced inwardly from the opposed rims of the seal housing; and
 a plurality of anchor members received in the through holes integral with the outer seal and with the inner seal for fixedly attaching the outer seal and the inner seal to the seal housing.

8. A system as set forth in claim 1
 wherein the header includes: a solid body portion containing the cylindrical bore; and
 a skirt member integral with the solid body portion and extending away therefrom to a lower rim which is the undersurface for mounting engagement on the mounting surface of the medical device.

9. A system for coupling a medical electrical lead to a medical device including a sealed housing containing a pulse generator for delivering electrical stimuli to body tissue comprising:
 a mounting surface on the sealed housing of the medical device and at least one electrically conductive feedthrough carried by the sealed housing coupled to the pulse generator and projecting beyond the mounting surface;
 a pre-molded header of non-conductive material having an outer peripheral surface, an undersurface for mounting engagement on the mounting surface of the medical device, an elongated cylindrical bore therein having a longitudinal axis and an inner peripheral surface extending between a terminal sealed end and a bore entrance at the outer peripheral surface;
 a plurality of pairs of seal assemblies and contact assemblies positioned, sequentially, in side by side relationship, in the elongated cylindrical bore, a last one of the seal assemblies being nearest the bore entrance;

a strain relief zone positioned in the elongated cylindrical bore of the header and fixed thereto and comprising an annular shoulder engaged with the last one of the seal assemblies and an annular rim spaced from the annular shoulder and facing the elongated bore entrance such that with force applied on the annular rim of the strain relief zone along the longitudinal axis toward the terminal sealed end, the plurality of pairs of seal assemblies and contact assemblies and the strain relief zone become firmly, sealingly, held between the proximal annular surface and the terminal sealed end, the plurality of pairs of seal assemblies and contact assemblies and the strain relief zone together defining a central passage;

the header having an aperture extending between the outer peripheral surface and the inner peripheral surface aligned with one of the contact assemblies; and at least one conductor wire electrically connecting the feedthrough and the one contact assembly;

wherein electrical contact is made between the one contact assembly and an associated terminal on the electrical lead inserted through the bore entrance into the cylindrical bore of the header.

10. A system as set forth in claim 9 wherein each contact assembly includes;

an annular housing defining an interior space, the housing including a tubular wall having an outer surface facing the interior space and an inner surface defining a central opening adapted to receive an electrical contact, the wall defining at least one aperture; and a garter spring contained within the interior space of the housing, the garter spring having an inner diameter, the garter spring encircling the outer surface of the wall under preload so that a portion of the inner diameter of the spring projects through the at least one aperture into the central opening of the housing for engaging an electrical contact received within the central opening.

11. A system as set forth in claim 10 wherein the at least one aperture comprises at least one slot extending circumferentially along the wall of the housing.

12. A system as set forth in claim 9 wherein the header has a channel in the outer peripheral surface extending from the aperture toward the mounting surface, the conductor wire received in the channel.

13. A system as set forth in claim 9 wherein the header includes:

a solid body portion containing the cylindrical bore; and a skirt member integral with the solid body portion and extending away therefrom to a lower rim which is the undersurface for mounting engagement on the mounting surface of the medical device.

14. A system as set forth in claim 9 wherein the header is composed of biocompatible thermoplastic material.

15. A connector assembly for coupling an electrical lead to an electrically energized device having a plurality of electrical terminals comprising:

a header of non-conductive material having an outer peripheral surface, an elongated cylindrical bore therein with a longitudinal axis, and an inner peripheral surface extending between a terminal sealed end and a bore entrance;

a block member insert molded into the header having a through bore coaxial with the cylindrical bore of the housing member;

a plurality of pairs of seal assemblies and contact assemblies positioned, sequentially, in side by side relationship, in the cylindrical bore of the header, a first one of the seal assemblies being proximate the block member, a last one of the seal assemblies being nearest the bore entrance, each contact assembly having electrical commonality with a terminal of the electrically energized device; and a strain relief zone positioned in the cylindrical bore of the header and fixed thereto and including an annular shoulder engaged with the last one of the seal assemblies and an annular rim spaced from the annular shoulder and facing the bore entrance such that with force applied on the annular rim of the strain relief zone along the longitudinal axis toward the block member, the plurality of pairs of seal assemblies and contact assemblies and the strain relief zone become firmly, sealingly, held between the proximal annular surface and the terminal sealed end, the plurality of pairs of seal assemblies and contact assemblies and the strain relief zone together defining a central passage coaxial with the through bore of the block member and extending between the block member and the bore entrance;

wherein electrical contact is made among each of a plurality of terminals on the electrical lead inserted through the bore entrance into the cylindrical bore of the housing member, an associated contact assembly, and an associated terminal of the electrically energized device.

16. A connector assembly as set forth in claim 15 wherein with adhesive applied between the strain relief zone and the bore of the header, the strain relief zone is permanently affixed to the header.

17. A connector assembly as set forth in claim 15 wherein the header includes:

a solid body portion containing the cylindrical bore;

wherein the header has a plurality of longitudinally spaced apertures aligned with each of the contact assemblies and extending between the outer peripheral surface and the inner peripheral surface, one of the electrical terminals of the electrically energized device received in each of the apertures.

18. A connector assembly as set forth in claim 17 wherein the header is composed of biocompatible thermoplastic material.

19. A system as set forth in claim 1 wherein the header further comprises:

a plurality of apertures extending between the outer peripheral surface and the inner peripheral surface, each of the apertures aligned with one of the contact assemblies;

a plurality of spaced channels at the outer peripheral surface; and conductor wires disposed within the plurality of spaced channels and the plurality of apertures, one of the conductor wires electrically connecting one of the electrically conductive feedthrough with one of the contact assemblies.

20. A system as set forth in claim 9 wherein the header further comprises a plurality of spaced channels at the outer peripheral surface, and wherein the at least one conductor wire is disposed within one of the plurality of spaced channels to electrically connect the feedthrough and the contact assembly.

21. A system as set forth in claim 9
wherein the inner peripheral surface of the cylindrical bore has a tapped surface adjacent the bore entrance; and
including:
an externally threaded annular compression sleeve slidably received on and coaxial with the strain relief zone and threadedly engaged with the inner peripheral surface of the elongated cylindrical bore adjacent the bore entrance, the compression sleeve extending between a proximal annular surface and a distal annular surface, the proximal annular surface engaged with the annular shoulder of the strain relief zone, such that with rotation of the compression sleeve in one direction about the longitudinal axis, the pair of seal assemblies, the contact assembly, and the strain relief zone become firmly held between the proximal annular surface and the terminal sealed end.

22. A connector assembly as set forth in claim 15
wherein the header further comprises:
a plurality of apertures extending between the outer peripheral surface and the inner peripheral surface of the header, each of the apertures aligned with one of the contact assemblies;
a plurality of spaced channels at the outer peripheral surface; and
conductor wires disposed within the plurality of spaced channels and the plurality of apertures and electrically connecting the associated contact assembly with the associated terminal of the electrically energized device.

* * * * *